United States Patent
Tanji

(10) Patent No.: US 7,815,861 B2
(45) Date of Patent: Oct. 19, 2010

(54) ANALYSIS METHOD, ANALYSIS DEVICE AND PRODUCTION METHOD THEREFOR

(75) Inventor: Hideki Tanji, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 10/530,725

(22) PCT Filed: Oct. 7, 2003

(86) PCT No.: PCT/JP03/12849

§ 371 (c)(1),
(2), (4) Date: Jan. 27, 2006

(87) PCT Pub. No.: WO2004/034040

PCT Pub. Date: Apr. 22, 2004

(65) Prior Publication Data

US 2006/0153738 A1    Jul. 13, 2006

(30) Foreign Application Priority Data

Oct. 8, 2002    (JP)    ............................. 2002-294448

(51) Int. Cl.
G01N 21/00    (2006.01)
G01N 21/76    (2006.01)
G01N 21/64    (2006.01)

(52) U.S. Cl. .............. 422/82.05; 422/82.06; 422/82.07; 422/82.08; 422/82.09; 436/164; 436/172

(58) Field of Classification Search .............. 422/82.05, 422/68.1, 82.09; 435/22
See application file for complete search history.

(56) References Cited

U.S. PATENT DOCUMENTS

| 4,986,665 A | 1/1991 | Yamanishi et al. |
| 5,259,381 A | 11/1993 | Cheung et al. |
| 5,780,304 A * | 7/1998 | Matzinger et al. ........... 436/169 |

FOREIGN PATENT DOCUMENTS

| EP | 1 118 859 | 7/2003 |
| JP | 4-60447 | 2/1992 |
| JP | 10-505676 | 6/1998 |
| JP | 2000-105196 | 4/2000 |
| JP | 2002-40022 | 2/2002 |
| WO | WO 96/07908 | 3/1996 |

* cited by examiner

*Primary Examiner*—Jill Warden
*Assistant Examiner*—Neil Turk
(74) *Attorney, Agent, or Firm*—Hamre, Schumann, Mueller & Larson, P.C.

(57) ABSTRACT

The present invention relates to a technique for analyzing the concentration of a specific component in a sample liquid, such as a method for analyzing a sample. The analyzing method includes a first detection step for irradiating light from a light source (50) onto a reaction system to detect a response from the reaction system (56) as a first detection result. The reaction system contains a sample liquid and a reagent. The method also includes a second detection step for irradiating light onto a reference board (54) to detect a response from the reference board as a second detection result. The response from the reference board under light irradiation is dependent on wavelength. The method further includes a calculation step for calculating the concentration of the specific component in the sample liquid based on the first and second detection results.

11 Claims, 6 Drawing Sheets

ANALYSIS METHOD, ANALYSIS DEVICE AND PRODUCTION METHOD THEREFOR

TECHNICAL FIELD

The present invention relates to a technique for analyzing the concentration of a specific component in a sample liquid.

BACKGROUND ART

An optical method is utilized to determine the quantity of a specific component in a sample liquid such as urine or blood. In this method, a reaction system including a sample liquid and a coloring substance is irradiated with light, and amount of reflected light, transmitting light, or scattering light is measured as a response from the reaction system. The measured amount of light is compared with a predetermined calibration curve to calculate the concentration of the specific component.

In an optical method, a difference in the concentration of a specific component between different sample liquids needs to be reflected as a relatively large difference between measured amounts of light for providing a high resolution. Thus, light selected to be irradiated onto the reaction system needs to have a wavelength which shows large light absorbance at the reaction system (more specifically, a reaction product between the specific component and the coloring reagent). For example, p-nitroaniline or p-nitrophenol may be used as a coloring substance which is irradiated with light having a wavelength of 450 nm to determine the concentration of GGT (gamma glutamyl transpeptidase), ALP (alkaline phosphatase), and Amy (amylase) based on the response from the coloring substance. For this purpose, light emitted from a light source is caused to pass through a wavelength selecting filter where a light component having a specific wavelength is extracted for irradiation onto the reaction system.

An example of wavelength selecting filter is an interference filter. The interference filter utilizes interference occurring at a transparent thin film having a thickness nearly equal to a desired wavelength of light, for transmitting or reflecting a light component with the desired wavelength. The transparent thin film may be formed by vapor deposition for example. Therefore, even if an attempt is made to produce thin films, there will be some degree of variations in selectable wavelength due to thickness variations of the product films. Improvement in measurement accuracy requires an interference filter having a reduced variation in selectable wavelength. As a result, interference filters having a large extent of errors cannot be used, which causes a problem that the production yield of interference filters reduces to result in a cost increase.

On the other hand, an example of light source for light irradiation is an LED which emits light having a temperature-dependent wavelength. Thus, the wavelength of emitted light changes due to a rise of environmental measurement temperature or due to a temperature rise of the actuated LED itself. Such a change in wavelength ranges to about ±10 nm of the peak wavelength.

The above-described variation or change in the peak wavelength affects the measured amount of light from the reaction system. As schematically shown in FIG. 9 with respect to GGT for example, even if the absorbance is constant at the reaction system, the calculation result largely varies as the measurement wavelength varies. Therefore, the measurement accuracy lowers due to irregularities of the measurement wavelength. This fact can be seen also from the simulation graph shown in FIG. 10.

FIGS. 10A-10C illustrate the results of simulation with respect to GGT, ALP, and Amy, taking the relationship between wavelength deviations from the wavelength setting and measurement errors when the measurement wavelength is set at 405 nm. As seen from the figures, the measurement error increases as the deviation from the wavelength setting increases, regardless of the concentration of the measured component.

DISCLOSURE OF THE INVENTION

An object of the present invention is to determine the quantity of a specific component in a sample liquid by an optical method with high accuracy, even if the wavelength of light irradiated onto a reaction system deviates from an intended wavelength.

A first aspect of the present invention provides an analyzing method which comprises: a first detection step for irradiating light onto a reaction system to detect a response from the reaction system as a first detection result, the reaction system including a sample liquid and a reagent; a second detection step for irradiating light onto a reference board to detect a response from the reference board as a second detection result, the response from the reference board being dependent on wavelength; and a calculation step for calculating a concentration of a specific component in the sample liquid based on the first and second detection results.

The calculation step includes selecting a most suitable calibration curve from a plurality of pre-created calibration curves based on the second detection result, and calculating the concentration of the specific component based on the selected calibration curve and the first detection result. The calculation step may further include correcting the first detection result based on the second detection result, and calculating the concentration of the specific component based on the correction and the calibration curve. Alternatively, the calculation step may include performing primary calculation of the concentration of the specific component, and obtaining a final calculated value by correcting the primary calculated value.

At least one of the responses in the first and second detection steps is detected as an amount of regular reflection light, transmitting light, or scattering reflection light, for example.

A second aspect of the present invention provides an analyzing device which comprises a light irradiator; a detector for detecting a first response from a reaction system under light irradiation from the light irradiator, the reaction system including a sample liquid and a reagent, the detector detecting a second response from a reference board under light irradiation from the light irradiator, the second response from the reference board being dependent on wavelength; and a calculator for calculating a concentration of a specific component in the sample liquid based on the first and second responses.

The analyzing device may further comprise a storage for storing a plurality of calibration curves each representing relationship between a first detection result corresponding to the first response and the concentration of the specific component, and a selector for selecting a most suitable calibration curve for calculation from the plurality of calibration curves based on a second detection result corresponding to the second response. The calculator calculates the concentration of the specific component based on the calibration curve selected by the selector and the first detection result.

The calculator may correct the first detection result corresponding to the first response based on the second detection result corresponding to the second response, and then calculates the concentration of the specific component based on the correction. The calculator may perform primary calculation of the concentration of the specific component based on the first detection result, and then calculates a final value by correcting the primary calculated value.

Preferably, the analyzing device of the present invention may further include a controller for controlling timing for detection of the second response at the detector. The controller may control the detector for detecting the second response before or after the detection of the first response. Of course, the controller may control the detector for detecting the second response simultaneously with the detection of the first response. The controller may also control the detector for detecting the second response upon start-up of the analyzing device.

The light irradiator may comprise a light source. Examples of the light source include an LED and a halogen lamp. The light irradiator may further include a filter, such as an interference filter or colored filter, for selecting the wavelength of emitted light.

At least one of the first and second responses may be detected as an amount of regular reflection light, transmitting light, or scattering reflection light.

A third aspect of the present invention provides a method of producing an analyzing device which comprises a light irradiator for irradiating light onto a reaction system which includes a sample liquid and a reagent, a detector for detecting a response from the reaction system under light irradiation, a calculator for calculating a concentration of a specific component in the sample liquid based on the detection at the detector, and a storage for storing information necessary for calculation as to the specific component. The method comprises: a detection step for irradiating light from the light irradiator onto a reference board to detect a response from the reference board under light irradiation for determining a light emitting state of the light irradiator, the response from the reference board being dependent on wavelength; and a storage step for storing the light emitting state in the storage as information for use in calculation at the calculator.

The analyzing device production method may further comprise a calibration curve selecting step for selecting a calibration curve corresponding to the light emitting state, from a plurality of calibration curves representing relationship between the detection result at the detector and the concentration of the specific component, based on the detection in the detection step. In this case, the storage step includes storage of the calibration curve selected in the calibration curve selecting step for use in calculation at the calculator.

The light emitting state is detected as a peak wavelength of emitted light in the detection step, and the peak wavelength is stored by the storage in the storage step. In this case, a plurality of calibration curves may be stored in the storage in advance, and a most suitable calibration curve may be selected with reference to the peak wavelength stored in the storage for use in calculation at the calculator. The peak wavelength may be also used by the calculator to correct the calculated concentration, or to correct the detection result at the detector for calculating the concentration based on the corrected detection result.

The reference board used in the detection step may be incorporated in the analyzing device beforehand. Alternatively, the reference board may be prepared separately from the analyzing device.

BEST MODE FOR CARRYING OUT THE INVENTION

Figure 1:
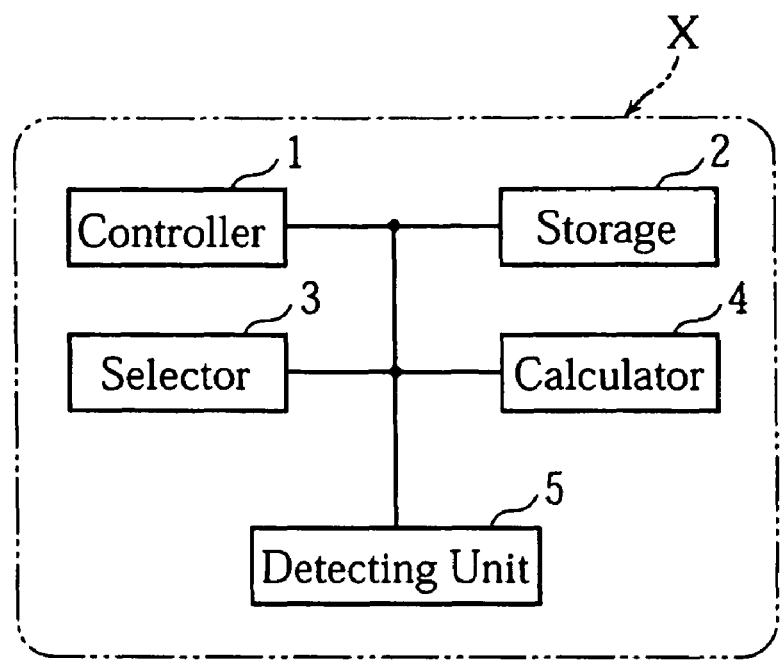
FIG. 1 is a block diagram showing an analyzing device according to the present invention.

An analyzing device X shown in FIG. 1 includes a controller 1, a storage 2, a selector 3, a calculator 4, and a detecting unit 5.

The controller 1 controls the elements 2-5 based on a control program stored in the storage 2.

Figure 2:
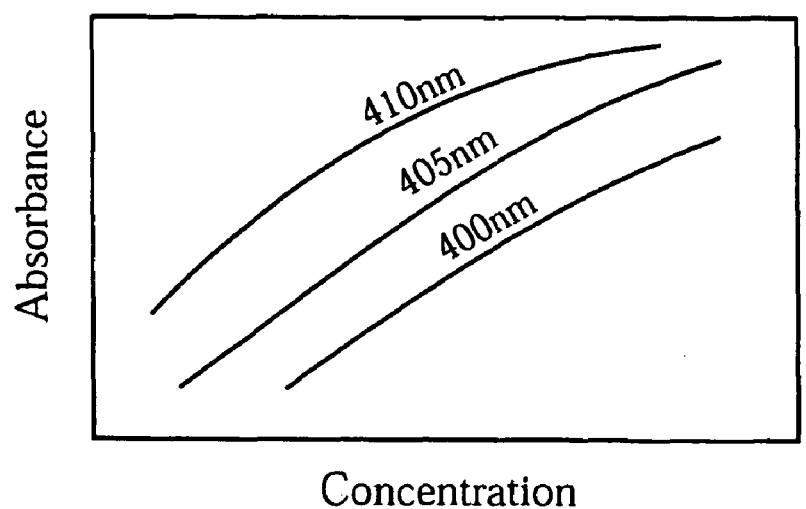
FIG. 2 is a graph illustrating concentration-absorbance relationship with respect to a plurality of measurement wavelengths.

The storage 2 stores information which includes a plurality of calibration curves corresponding to various programs or measurement wavelengths, while also storing information used for correcting measured values and calculated values. As shown in FIG. 2, the calibration curves represent the relationship between the light absorbance and the concentration of a specific component. The information regarding the calibration curves is stored as mathematical formulas or tables. According to the present embodiment, a plurality of calibration curves are stored in the storage 2 in consideration of and in corresponding relationship to possible deviations of measurement wavelength.

The selector 3 shown in FIG. 1 selects a calibration curve, which best fits to the actual measurement wavelength, out of the calibration curves stored in the storage 2 based on the detection at the detecting unit 5.

The calculator 4 performs calculation necessary for analyzing the specific component in the sample liquid based on the detection at the detecting unit 5 and on the calibration curve selected by the selector 3.

Figure 3:
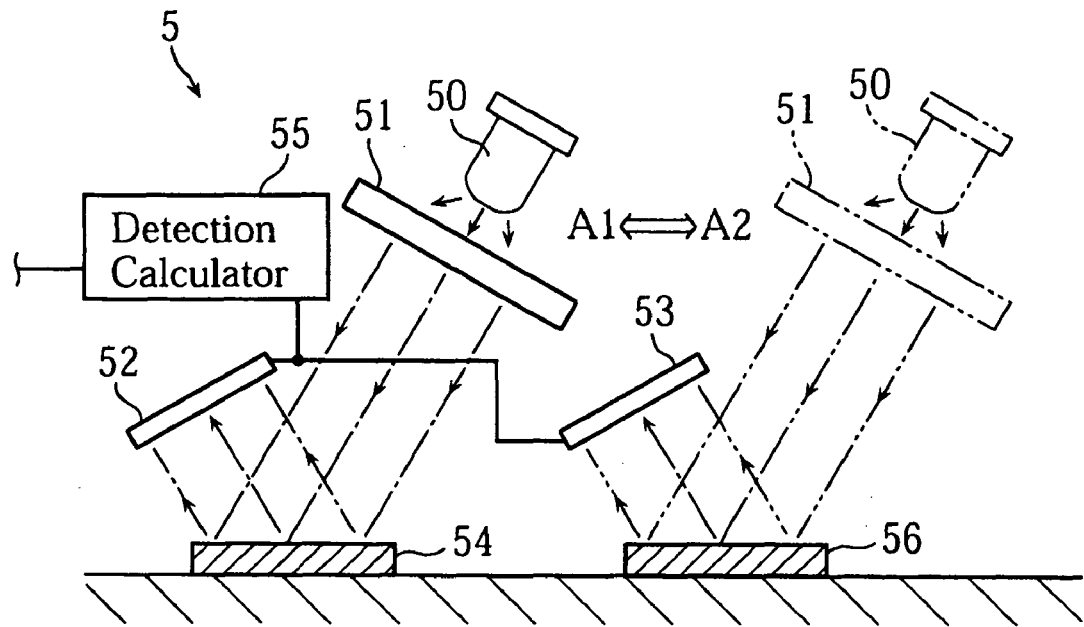
FIG. 3 is a schematic diagram illustrating a detecting unit of the analyzing device shown in FIG. 1.

As shown in FIG. 3, the detecting unit 5 includes a light source 50, a wavelength selecting filter 51, a first and a second light-sensitive elements 52, 53, a reference board 54, and a detection-calculator 55. The detecting unit is designed to support an analytical piece 56 supplied with a sample liquid.

The light source 50 is movable in directions A1 and A2 in the figure for light irradiation onto the reference board 54 and the analytical piece 56. The light source 50 may be an LED, for example. Alternatively, the light source may be provided by another light emitting medium such as a halogen lamp.

The wavelength selecting filter 51 extracts a light component of a specific wavelength from the light rays emitted by the light source 50, and is movable with the light source 50 in the directions A1 and A2 in the figure. The wavelength selecting filter 51 may comprise an interference filter or a color filter, for example.

If the analyzing device X is designed to test a plurality of items, use may be made of a plurality of wavelength selecting filters each having a different wavelength selectivity. The light source and the wavelength selecting filter are not necessarily movable. Instead, plural sets of a light source and one or more wavelength selecting filters may be provided, or, a set of a light source and one or more wavelength selecting filters may be provided at a fixed position from which the light passing through the wavelength selecting filter is selectively guided to a plurality of portions utilizing optical fibers, for example. If the light source is able to emit light of a single wavelength, the wavelength selecting filter may be omitted.

The first light-sensitive element 52 receives light reflected by the reference board 54, whereas the second light-sensitive element 53 receives light reflected by the analytical piece 56. The light-sensitive elements 52, 53 may comprise photodiodes, for example.

Figure 4:
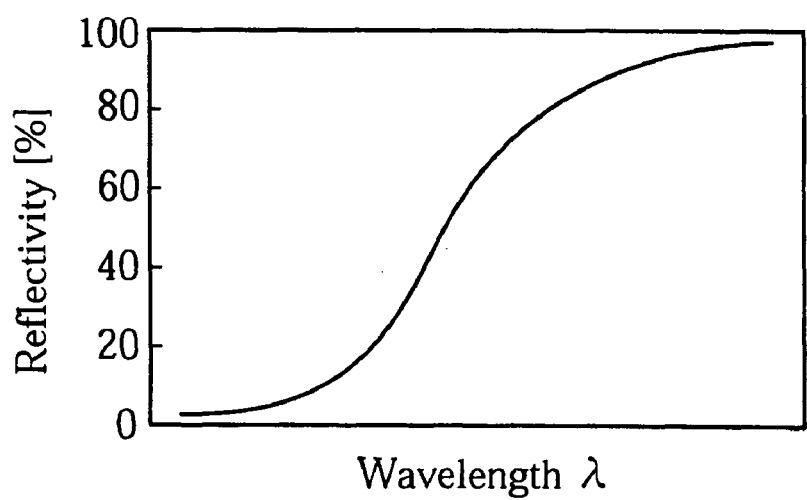
FIG. 4 is a graph illustrating an example of relationship between the wavelength of irradiated light and the reflectivity of a reference board.

As shown in FIG. 4, the reference board 54 is so designed that the reflectivity at the surface of the reference board depends on the wavelength of light irradiated thereon. In other words, measurement of the reflectivity of light irradiated onto the reference board 54 enables measurement of the wavelength of light irradiated on the reference board 54.

The detection-calculator 55 shown in FIG. 3 calculates the reflectivity or the wavelength of light irradiated onto the reference board 54 based on the amount of light received at the first light-sensitive element 52, while also calculating the light absorbance at the analytical piece 56 based on the amount of light received at the second light-sensitive element 53. However, the detection-calculator 55 may be omitted and the calculator 4 may play the role of the calculation portion 55.

Each of the controller 1, storage 2, selector 3, calculator 4, and detection-calculator 55 may be provided by one or a combination of CPU, ROM, and RAM. Alternatively, the above-described elements may be provided collectively by a single CPU connected to a plurality of memories.

Next, the function of the analyzing device X is described with reference to the flowcharts shown in FIGS. 5-8 in addition to FIGS. 1-3. It should be noted that checking of measurement wavelength need only be performed either upon power switch-on (start-up of the device) or upon concentration measurement. However, for purposes of the following description, checking of measurement wavelength is performed at both steps of switch-on and concentration measurement.

Figure 5:
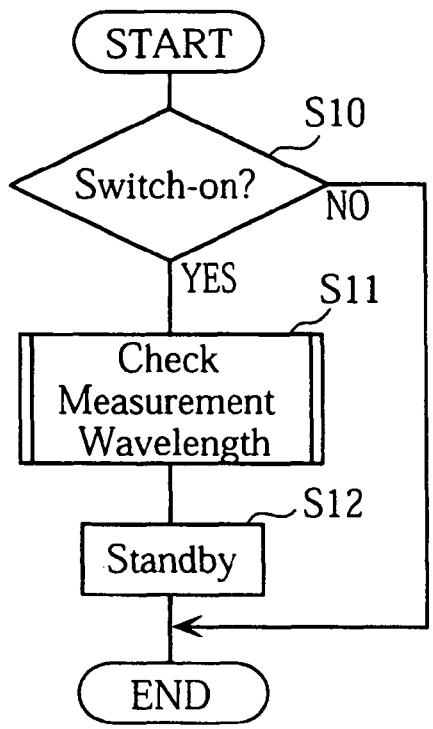
FIG. 5 is a flow chart illustrating the process for checking the measurement wavelength upon start-up of the analyzing device.

As shown in FIG. 5, on start-up of the analyzing device X, determination is made on whether the analyzing device X is switched on or not (S10). If the device is switched on (S10: YES), the respective electrical circuits are started up for checking measurement wavelength (S11).

Figure 6:
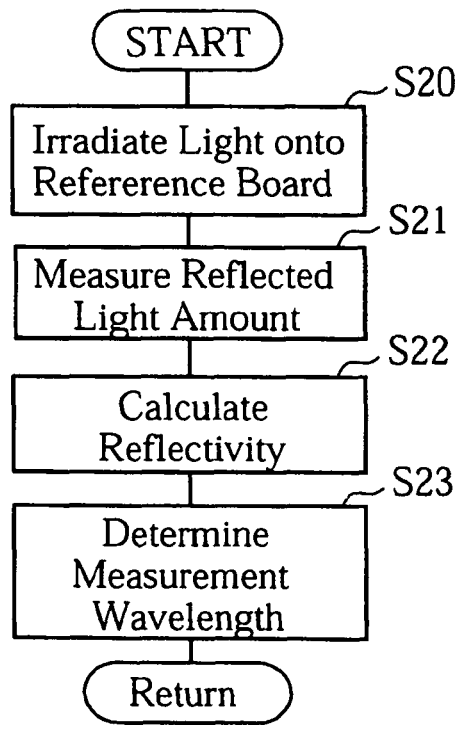
FIG. 6 is a flow chart illustrating the measurement wavelength checking process.

The checking of measurement wavelength is performed through the procedures shown in FIG. 6. First, the light source 50 is driven to emit light which passes through the wavelength selecting filter 51 for irradiation onto the reference board 54 (S20). The irradiated light is reflected by the reference board 54 and received by the first light-sensitive element 52 where the amount of the reflected light is measured (S21). The measured amount of the reflected light is detected by the detection-calculator 55. The detection-calculator 55 calculates the reflectivity at the reference board 54 based on the amount of the reflected light (S22).

As described above, the reflectivity at the surface of the reference board 54 has wavelength dependence. Thus, based on the reflectivity at the reference board 54, the detection-calculator 55 determines the wavelength of the light irradiated onto the reference board 54; that is, the wavelength of light (measurement wavelength) to be later irradiated onto the analytical piece 56 (S23). The relationship between the reflectivity and wavelength is stored in the storage 2 beforehand, for example, so that the measurement wavelength is determined based on the relationship stored in the storage 2 and on the calculated reflectivity. When the measurement wavelength is determined (S23), the analyzing device X is brought into a standby state (S12) as shown in FIG. 5, thereby finishing the start-up of the device.

Figure 7:
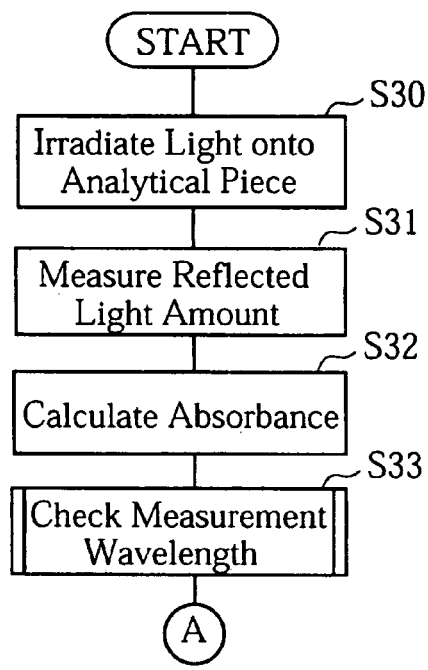
FIG. 7 is a flow chart illustrating concentration measurement at the analyzing device.
Figure 8A:
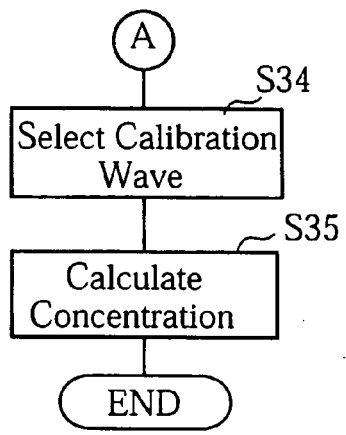
FIGS. 8A-8C are flow charts illustrating concentration measurement at the analyzing device.

Concentration measurement at the analyzing device X is performed through the procedures shown in FIGS. 7 and 8A.

As shown in FIG. 7, first, the light source 50 is driven to emit light, and the light from the light source 50 is caused to pass through the wavelength selecting filter 51 for irradiation onto the analytical piece 56 (S30). The irradiated light is reflected by the analytical piece 56 and received by the second light-sensitive element 53 where the amount of the light is measured (S31). The measured amount of the reflected light is detected by the detection-calculator 55, whereby the detection-calculator 55 calculates the absorbance at the analytical piece 56 based on the amount of the reflected light (S32).

Further, the detecting unit 5 checks the measurement wavelength (S33). The checking of the measurement wavelength is performed through the procedures similar to the ones described above with reference to FIG. 6. The checking of the measurement wavelength may be performed before or together with the absorbance calculation.

Next, as shown in FIG. 8A, based on the checked measurement wavelength, the selector 3 selects, among a plurality of calibration curves stored in the storage 2, a calibration curve which best fits to the check result (S34). The calculator 4 calculates the concentration based on the calculated absorbance and on the calibration curve selected by the selector 3 (S35).

Figure 8B:
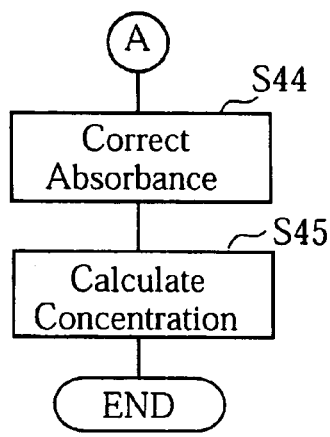
Figure 8C:
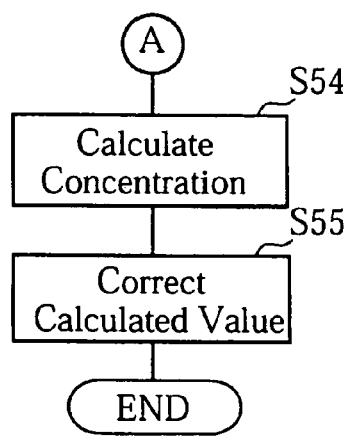
Figure 9:
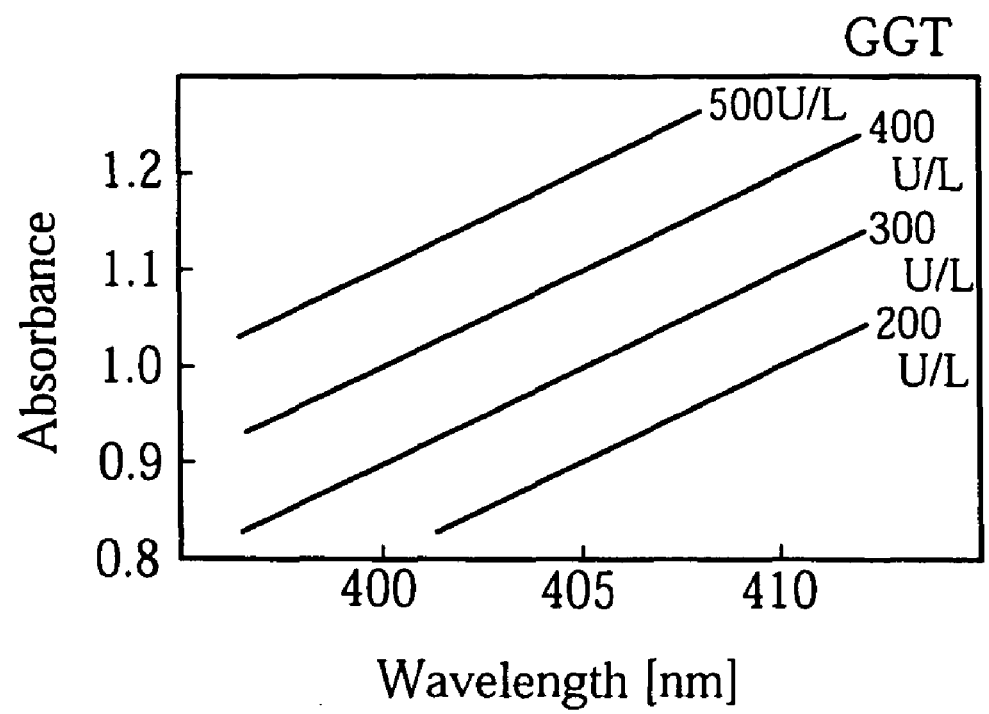
FIG. 9 is a graph illustrating relationship between the measurement wavelength and the absorbance with respect to a specific component (GGT) at a plurality of concentrations.
Figure 10A:
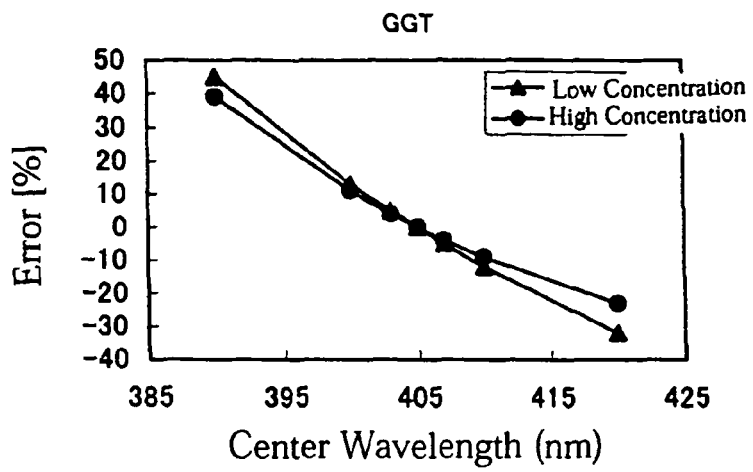
FIGS. 10A-10C are graphs illustrating relationship between the measurement wavelength and the measurement error.
Figure 10B:
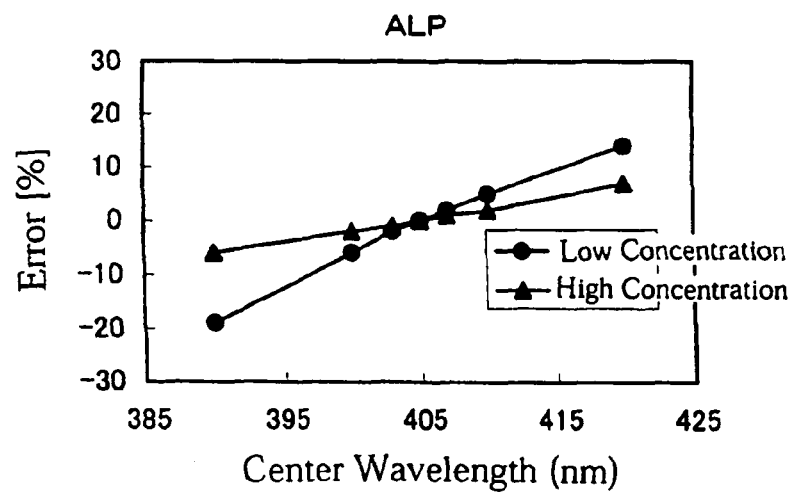
Figure 10C:
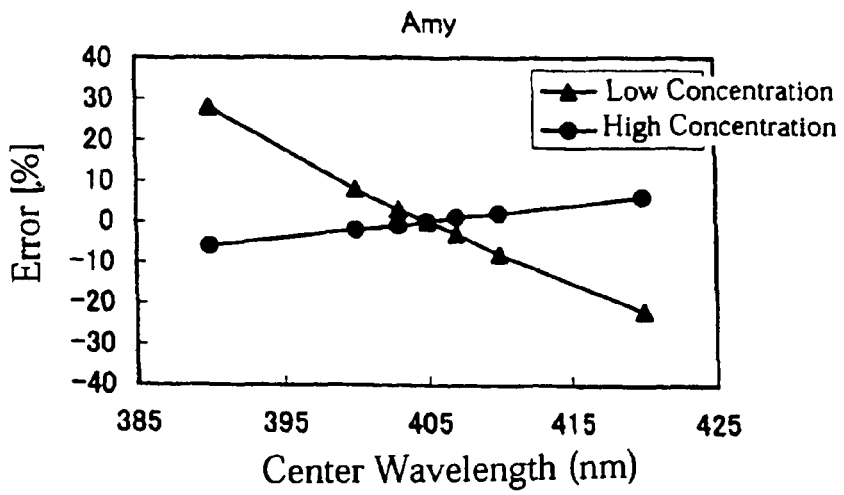

In concentration measurement, the steps S34 and S35 shown in FIG. 8A may be replaced with steps S44 and S45 shown in FIG. 8B or with steps S54 and S55 shown in FIG. 8C. It should be noted that, in the examples shown in FIGS. 8B and 8C, only one calibration curve is stored in the storage 4 with respect to each of the measurement items.

In the example shown FIG. 8B, the absorbance calculated at the detection-calculator 55 is corrected based on a predetermined wavelength checked by the detecting unit 5 (S44), and then the concentration is calculated based on the corrected absorbance and on the calibration curve stored in the storage 4 (S45). In the example shown in FIG. 8C, the concentration is calculated based on the absorbance calculated at the detection-calculator 55 and on the calibration curve stored in the storage 4 (S54), and then the calculated concentration is corrected based on the measurement wavelength checked by the detecting unit 5 (S55).

In the present embodiment, the measurement wavelength is checked at least either upon start-up of the analyzing device X or upon concentration measurement. Therefore, even if an actual measurement wavelength deviates from an expected measurement wavelength due to deterioration of e.g. the wavelength selecting filter or the light source, or due to production errors, such a deviation can be corrected for enabling concentration measurement with high accuracy.

If the measurement wavelength is checked upon start-up of the analyzing device X, there is no need to perform such checking upon every concentration measurement, whereby the measuring time is not increased by the checking of measurement wavelength. On the other hand, if the measurement wavelength is performed upon concentration measurement, a correction can be made to account for fluctuations of measurement wavelength due to environmental factors, or, when LED is used as a light source, due to a temperature increase of LED which causes wavelength fluctuations, thereby enabling concentration measurement with high accuracy.

In the present embodiment, is checked based on reflected light from the reference board. However, the measurement wavelength may also be checked based on light scattering from or transmitting through the reference board. Further, the absorbance at the analytical piece, which is used for calculation of the concentration, may also be calculated based on scattering or transmitting light. Further, when the measurement wavelength is checked based on reflected light from the reference board, checking of measurement wavelength may be performed directly using the amount of the reflected light without calculating the reflectivity before calculating the measurement wavelength. Similarly, the concentration may be calculated by using the amount of light (response) from the analytical piece, instead of using the absorbance at the analytical piece.

The above-described checking of the measurement wavelength at the analyzing device may be performed before shipment of the analyzing device.

The checking of the measurement wavelength before shipment is performed after, at the earliest, assembling the detecting unit which includes the light source and the light-sensitive element. In other words, the checking of the measurement wavelength may be performed after the entire analyzing device is made, or when the detecting unit is assembled for used. As described above, such checking of the measurement wavelength is performed using the reference board, and the reference board may be incorporated in the detecting unit for checking the measurement wavelength after shipment of the analyzing device. On the other hand, if the checking of the measurement wavelength is not performed after shipment of the analyzing device, a reference board for such checking may be prepared separately for use in subsequently checking the measurement wavelength.

After the checking of the measurement wavelength, a calibration curve which best fits to the checked measurement wavelength is selected from a plurality of calibration curves corresponding to various measurement wavelengths, and the selected calibration curve may be stored in the storage of the analyzing device. In this case, the plurality calibration curves may be stored in the storage beforehand, and a program is installed so that the selected calibration curve is used to perform calculation. Of course, only the selected calibration curve may be stored in the storage. Selection of a calibration curve which fits to the measurement wavelength may be performed directly using the amount of reflected light from the reference board without calculating the measurement wavelength.

Information regarding the measurement wavelength may be stored in the storage based on the response from the irradiated reference board. In this case, the analyzing device performs calculation at the calculator using the information regarding the measurement wavelength. Specifically, the analyzing device corrects the absorbance calculated by the detecting unit and then calculates the concentration based on the corrected absorbance, or calculates the concentration based on the absorbance and then corrects the calculated concentration.

In this way, checking of the measurement wavelength before shipment of the analyzing device removes the influences of production errors of the wavelength selecting filter or the light source in advance, thereby enabling to provide an analyzing device for calculating concentration with high accuracy.

The invention claimed is:

1. An analyzing method comprising:
   a relation determination step of determining a relationship between variations of reflectivity and variations of wavelength with respect to a reference board whose reflectivity varies continuously as the wavelength of light irradiated onto the reference board varies, the variations of the wavelength of irradiated light being caused by environmental temperature changes that also cause fluctuations of reflectivity;
   a first detection step of irradiating light onto a reaction system to detect an amount of light reflected from the reaction system as a first detection result, the reaction system including a sample liquid and a reagent;
   a second detection step of irradiating light onto the reference board to detect an amount of light reflected from the reference board as a second detection result; and
   a calculation step of calculating the wavelength of irradiated light based on the second detection result and the relationship between variations of reflectivity and variations of wavelength with respect to the reference board while also calculating a concentration of a specific component in the sample liquid based on the first detection result and the calculated wavelength of irradiated light.

2. The analyzing method according to claim 1, wherein the calculation step includes selecting a most suitable calibration curve from a plurality of pre-created calibration curves based on the second detection result, and calculating the concentration of the specific component based on the selected calibration curve and the first detection result.

3. The analyzing method according to claim 1, wherein the calculation step further includes correcting the first detection result based on the second detection result, and calculating the concentration of the specific component based on the correction and a calibration curve.

4. The analyzing method according to claim 1, wherein the calculation step further includes performing primary calculation of the concentration of the specific component, and obtaining a final calculated value by correcting the primary calculated value.

5. An analyzing device comprising:
   a storage that stores a relationship between variations of reflectivity and variations of wavelength with respect to a reference board whose reflectivity varies continuously as the wavelength of light irradiated onto the reference board varies, the variations of the wavelength of irradiated light being caused by environmental temperature changes that also cause fluctuations of reflectivity;
   a light irradiator for irradiating light toward a reaction system and the reference board, the reaction system including a sample liquid and a reagent;
   a detecting unit arranged to face the reaction system and the reference board for detecting an amount of light reflected from the reaction system under light irradiation from the light irradiator as a first detection result, the detecting unit detecting an amount of light reflected from the reference board under light irradiation from the light irradiator as a second detection result; and
   a calculator connected to the detecting unit and the storage configured to calculate the wavelength of irradiated light based on the second detection result and the predetermined relationship between variations of reflectivity and variations of wavelength with respect to the reference board while also configured to calculate a concentration of a specific component in the sample liquid based on the first detection result and the calculated wavelength of irradiated light.

6. The analyzing device according to claim 5,
wherein the storage also stores a plurality of calibration curves each representing a relationship between the first detection result and the concentration of the specific component;
the analyzing device further comprising a selector connected to the calculator and the storage for selecting a most suitable calibration curve for calculation from the plurality of calibration curves based on the second detection result;
the calculator configured to calculate the concentration of the specific component based on the calibration curve selected by the selector and the first detection result.

7. The analyzing device according to claim 5, wherein the calculator is configured to correct the first detection result based on the second detection result and is configured to calculate the concentration of the specific component based on the correction.

8. The analyzing device according to claim 5, wherein the calculator is configured to perform primary calculation of the concentration of the specific component based on the first detection result, and is configured to calculate a final value by correcting the primary calculated value.

9. The analyzing device according to claim 5, further comprising a controller connected to the detecting unit and the calculator configured to control timing for detection of the second detection result at the detector.

10. The analyzing device according to claim 9, wherein the controller is further configured to control the detector for detecting the second detection result before or after the detection of the first detection result, or simultaneously with the detection of the first detection result.

11. The analyzing device according to claim 9, wherein the controller is further configured to control the detector for detecting the second detection result upon start-up of the analyzing device.

* * * * *